(12) United States Patent
Sainani

(10) Patent No.: US 10,081,586 B2
(45) Date of Patent: Sep. 25, 2018

(54) PROCESS FOR THE SYNTHESIS OF 9,9-BIS(METHOXYMETHYL)FLUORENE

(71) Applicant: SABIC GLOBAL TECHNOLOGIES B.V., Bergen op Zoom (NL)

(72) Inventor: Jaiprakash Brijlal Sainani, Baroda (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/578,424

(22) PCT Filed: May 30, 2016

(86) PCT No.: PCT/EP2016/062165
§ 371 (c)(1),
(2) Date: Nov. 30, 2017

(87) PCT Pub. No.: WO2016/193212
PCT Pub. Date: Dec. 8, 2016

(65) Prior Publication Data
US 2018/0148397 A1 May 31, 2018

(30) Foreign Application Priority Data
Jun. 1, 2015 (EP) .................................... 15170078

(51) Int. Cl.
*C07C 41/16* (2006.01)
*C07C 43/168* (2006.01)
(52) U.S. Cl.
CPC .......... *C07C 41/16* (2013.01); *C07C 2603/18* (2017.05)

(58) Field of Classification Search
CPC ...................................................... C07C 41/16
See application file for complete search history.

(56) References Cited

FOREIGN PATENT DOCUMENTS

| CN | 1336359 A | * | 2/2002 |
| EP | 0728720 A1 | | 8/1996 |
| EP | 0728724 A1 | | 8/1996 |
| EP | 0728770 A1 | | 8/1996 |

OTHER PUBLICATIONS

Chen Lei et al., "Synthesis of 9,9'-Bis(methoxymethyl)fluorine"; Transactions of Tianjin University, 2003, vol. 9, Issue 3, pp. 226-227.
International Search Report for International Application No. PCT/EP2016/062165; dated Jul. 12, 2016; 3 pages.
Written Opinion of the International Search Report for International Application No. PCT/EP2016/062165; dated Jul. 12, 2016; 5 pages.

* cited by examiner

*Primary Examiner* — Paul A Zucker
(74) *Attorney, Agent, or Firm* — Cantor Colburn LLP

(57) ABSTRACT

The present invention relates to a novel process for the synthesis of 9,9-bis(methoxymethyl)fluorene. The syntheses from fluorene to 9,9-bis(hydroxymethyl)fluorene via a hydroxymethylation and further to 9,9-bis(methoxymethyl) fluorene via a etherification are known. 9,9-bis(methoxymethyl)fluorene is a compound that is used as an electron donor for Ziegler-Natta catalysts. The present invention is related to an improvement in the synthesis of 9,9-bis(methoxymethyl)fluorene leading to a decrease in the amount of solvent used and an easier work up while achieving high yield and purity.

14 Claims, No Drawings

PROCESS FOR THE SYNTHESIS OF 9,9-BIS(METHOXYMETHYL)FLUORENE

CROSS REFERENCE TO RELATED APPLICATIONS

This application is a 371 of International Application No. PCT/EP2016/062165, filed May 30, 2016, which claims priority to EP Application No. 15170078.8 filed Jun. 1, 2015, both of which are incorporated herein by reference in their entirety.

The present invention relates to a novel process for the synthesis of 9,9-bis(methoxymethyl)fluorene. The synthesis from fluorene via 9,9-bis(hydroxymethyl)fluorene to 9,9-bis(methoxymethyl)fluorene is known. 9,9-bis(methoxymethyl)fluorene is a compound that is used as an electron donor for Ziegler-Natta catalysts. The process for preparing this compound from fluorene typically comprises two separate steps, which are each discussed below.

Step 1 of the synthesis from fluorene to 9,9-bis(methoxymethyl)fluorene relates to the hydroxymethylation of fluorene to 9,9-bis(hydroxymethyl)fluorene. This hydroxymethylation is typically carried out using paraformaldehyde wherein dimethyl sulfoxide (DMSO) is used as a solvent. An alcoholic solution of sodium alkoxide, such as sodium methoxide in methanol or sodium ethoxide in ethanol is used as a base. Typically, first a solution or dispersion of paraformaldehyde, DMSO and sodium alkoxide is prepared. Then a solution or dispersion of fluorene is added to this mixture. The reaction is usually carried out at very low temperatures in an ice bath. But temperatures of e.g. between 12 and 15° C. have also been disclosed in the prior art. The reaction is usually worked up by quenching with hydrochloric acid, addition of water and then one or more steps of extraction, distillation and/or recrystallization.

EP 0 728 770 discloses a method using a large volume of DMSO and a reaction temperature of 0° C. Chen et al. "synthesis of 9,9'-bis(methoxymethyl)fluorene", Transactions of Tianjin University, 2003, volume 9, issue 3, pages 226-227 discloses that the reaction is carried out at a temperature of between 13 and 15° C. and requires a large volume of DMSO.

The method according to the prior art require large volumes of DMSO during the synthesis of 9,9-bis(hydroxymethyl)fluorene as well as large volume and water and solvents, such as toluene and/or ethyl acetate, during the work up of 9,9-bis(hydroxymethyl)fluorene which is undesirable from a cost as well as environmental view.

Step 2 of the synthesis from fluorene to 9,9-bis(methoxymethyl)fluorene relates to the etherification of 9,9-bis(hydroxymethyl)fluorene to 9,9-bis(methoxymethyl)fluorene. According to some prior art documents a combination of methyl iodide and sodium hydride is used, e.g. in EP 0 728 770. In Chen et al. a different process is disclosed using sodium hydroxide solution and dimethyl sulfate as the alkylating agent and a tetrabutylammonium bromide phase transfer agent.

The methods according to the prior art however lead to the partial decomposition of DMS during the reaction which will reduces the strength of alkali solution. This will lead to a lower yield.

It is an aim of the present invention to overcome these drawbacks of the prior art during the synthesis of 9,9-bis(hydroxymethyl)fluorene.

In is another aim of the present invention to provide a process for preparing 9,9-bis(methoxymethyl)fluorene in a high yield.

In is another aim of the present invention to provide a process for preparing 9,9-bis(methoxymethyl)fluorene having a high purity.

One or more of these aims are achieved by a process according to the present invention.

SUMMARY

The present invention is related in a first aspect to a process for the synthesis of 9,9-bis(hydroxymethyl)fluorene from fluorene comprising providing a mixture of paraformaldehyde, dimethylsulfoxide and a sodium alkoxide and adding fluorene to said mixture to obtain 9,9-bis(hydroxymethyl)fluorene, wherein fluorene is added as a solid.

In an embodiment of said first aspect, fluorene is added in the form of a powder.

In an embodiment of said first aspect, dimethylsulfoxide is present in an amount of at most 1250 milliliters per mole of fluorene used. In an embodiment of said first aspect, dimethylsulfoxide is present in an amount of at most 1000 milliliters per mole of fluorene used. In an embodiment of said first aspect, dimethylsulfoxide is present in an amount of at most 700 milliliters per mole of fluorene used.

In an embodiment of said first aspect, paraformaldehyde is used in an amount of between 1.8 and 2.6 mole per mole of fluorene used.

In an embodiment of said first aspect, the sodium alkoxide is selected from sodium methoxide and sodium ethoxide. In an embodiment of said first aspect, the sodium alkoxide is sodium methoxide. In an embodiment of said first aspect, the sodium alkoxide is used as a sodium alkoxide solution in an alcoholic solution. In an embodiment of said first aspect, the sodium alkoxide is used as a sodium alkoxide solution in an alcoholic solution selected from sodium methoxide in methanol or sodium ethoxide in ethanol. In an embodiment of said first aspect, sodium alkoxide is used as a sodium alkoxide solution in an alcoholic solution, being sodium methoxide in methanol.

In an embodiment of said first aspect, said process comprises the following steps:
a) providing a mixture of paraformaldehyde and dimethylsulfoxide;
b) adding a sodium alkoxide solution in an alcoholic solvent to the mixture of step a);
c) adding fluorene as a solid to the mixture obtained in step b);
d) allowing the mixture obtained in step c) to react;
e) quenching the mixture obtained in step d) by adding an acid;
f) mixing the mixture obtained in step e) with water to obtain a suspension of crude 9,9-bis(hydroxymethyl)fluorene;
g) filtering said mixture of step f) to obtain crude 9,9-bis(hydroxymethyl)fluorene.

In an embodiment of said first aspect, the crude 9,9-bis(hydroxymethyl)fluorene obtained in step g) is recrystallized to obtain 9,9-bis(hydroxymethyl)fluorene.

In an embodiment of said first aspect, the acid used to quench the mixture in step e) is an inorganic acid. In an embodiment of said first aspect, the acid used to quench the mixture in step e) is hydrochloric acid. In an embodiment of said first aspect, the acid used to quench the mixture in step e) is concentrated hydrochloric acid.

In an embodiment of said first aspect, water is added during step f) in an amount of between 1250 and 5000 milliliters water per mole of fluorene used.

In an embodiment of said first aspect, the process is carried out at a temperature between 10 and 20° C.

In an embodiment of said first aspect, the process comprises the following steps:
  a) providing a mixture of between 1.8 and 2.6 mole of paraformaldehyde per mole of fluorene used and at most 1250 milliliters of dimethylsulfoxide per mole of fluorene used;
  b) adding a sodium alkoxide solution in an alcoholic solvent to the mixture of step a) so that the amount of sodium alkoxide is between 0.2 and 0.3 mole per mole of fluorene used;
  c) over a period of between 5 and 30 minutes adding fluorene in the form of a powder to the mixture obtained in step b) at a temperature between 10 and 20° C.;
  d) allowing the mixture obtained in step c) to react for a period of between 10 and 50 minutes at a temperature of between 10 and 20° C.;
  e) quenching the mixture obtained in step d) by adding an acid in an amount of between 10 and 20 milliliters per mole of fluorene used;
  f) mixing the mixture obtained in step e) with water in an amount of between 1250 and 5000 milliliters water per mole of fluorene used for a period of between 10 and 50 minutes to obtain a suspension of crude 9,9-bis(hydroxymethyl)fluorene;
  g) filtering said mixture of step f) to obtain crude 9,9-bis(hydroxymethyl)fluorene;
  h) optionally recrystallizing said crude reaction product from toluene in an amount of between 400 and 1250 milliliter per mole of fluorene used by heating said crude reaction product and toluene to a temperature between 60 and 110° C., cooling said mixture to a temperature of between 0 and 20° C. and then stirring said mixture at a temperature of between 0 and 20° C. for a period of between 30 and 240 minutes;
  i) optionally filtering said mixture of h) to obtain 9,9-bis(hydroxymethyl)fluorene.

The present invention is related in a second aspect to a process for the synthesis of 9,9-bis(methoxymethyl)fluorene from 9,9-bis(hydroxymethyl)fluorene comprising providing an alkali metal hydroxide solution, mixing said solution with tetraalkylammonium halide, 9,9-bis(hydroxymethyl)fluorene and a solvent and adding dimethyl sulfate to obtain 9,9-bis(methoxymethyl)fluorene wherein dimethyl sulfate is added in at least three portions wherein the reaction mixture is stirred for a period of at least 60 minutes before the following portion is added.

In an embodiment of said second aspect, said 9,9-bis(hydroxymethyl)fluorene is prepared according to the process in the first aspect of the present invention. However, 9,9-bis(hydroxymethyl)fluorene may also be obtained by other methods or may be commercially obtained.

In an embodiment of said second aspect, as the alkali metal hydroxide, sodium hydroxide is used. In an embodiment of said second aspect, as the alkali metal hydroxide, sodium hydroxide is used as a 40 to 50 wt. % solution in water.

In an embodiment of said second aspect, the halide in the tetraalkylammonium halide is selected from the group consisting of chloride, bromide, fluoride, iodide and is preferably bromide. The bromide is preferred because it is widely available.

In an embodiment of said second aspect, the alkyl groups in the tetraalkylammonium halide are each independently selected from the group of C1-C12 alkyl, preferably C2-C8 alkyl, more preferably C3-C5 alkyl, such as n-propyl, iso-propyl, n-butyl, iso-butyl, tert-butyl, n-pentyl, sec-pentyl, tert-pentyl, 3-pentyl, isopentyl, neopentyl, most preferably an n-alkyl, such as n-butyl. Preferably, all the alkyl groups are the same.

In an embodiment of said second aspect, as the tetraalkylammonium halide tetra-n-butylammonium bromide is used.

In an embodiment of said second aspect, dimethyl sulfate is added in at least four portions. In an embodiment of said second aspect, dimethyl sulfate is added in at least five portions. In an embodiment of said second aspect, dimethyl sulfate is added in a total amount of between 2 and 6 moles per mole of 9,9-bis(hydroxymethyl)fluorene used.

In an embodiment of said second aspect, as the solvent toluene is used.

In an embodiment of said second aspect, said process comprises the steps of
  i) providing a solution of sodium hydroxide in water;
  ii) adding to the solution of step i) 9,9-bis(hydroxymethyl)fluorene, tetraalkylammonium halide and a solvent;
  iii) stirring the mixture obtained in step ii);
  iv) adding dimethyl sulfate in at least three portions, wherein the resulting reaction mixture obtained is stirred for a certain period of time before the following portion is added;
  v) continue stirring the reaction mixture obtained in iv);
  vi) adding water to the mixture obtained in step v) and stirring;
  vi) separate the mixture obtained in step vi) in an organic layer and a water layer, obtain the organic layer and wash the organic layer with water;
  vii) separate the mixture obtained in step vii) in an organic layer and a water layer, obtain the organic layer and remove the solvent to obtain crude 9,9-bis(methoxymethyl)fluorene.

In an embodiment of said second aspect, the crude 9,9-bis(methoxymethyl)fluorene obtained in step vii) is recrystallized to obtain 9,9-bis(methoxymethyl)fluorene.

In an embodiment of said second aspect, in step iv) each portion of dimethyl sulfate is added over a period of between 15 and 60 minutes.

In an embodiment of said second aspect, in step iv) between the addition of each portion the reaction mixture is stirred for a period of between 60 and 120 minutes.

In an embodiment of said second aspect, step v) is carried out for a period of between 16 and 30 hours.

In an embodiment of said second aspect, step iv) and/or step v) are carried out at a temperature of between 15 and 35° C.

In an embodiment of said second aspect, said process comprises the steps of
  i) providing a solution of between 40 and 50 wt. % of sodium hydroxide in water so that between 2.5 and 7.5 mole of sodium hydroxide is present per mole of 9,9-bis(hydroxymethyl)fluorene used;
  ii) adding to the solution in step i) 9,9-bis(hydroxymethyl)fluorene, tetra-n-butylammonium bromide in an amount of 0.005 and 0.025 mole per mole of 9,9-bis(hydroxymethyl)fluorene used and adding toluene in an amount of between 800 and 1500 milliliter per mole of 9,9-bis(hydroxymethyl)fluorene used;
  iii) stirring the mixture obtained in step ii) for a period of between 1 and 5 hours at a temperature between 15 and 30° C.;
  iv) adding dimethyl sulfate in a total amount of between 2 and 6 moles per mole of 9,9-bis(hydroxymethyl)

fluorene in between 3 to 6 portions, wherein each portion is added over a period of between 15 and 60 minutes and wherein the resulting reaction mixture is stirred for a period of between 60 and 120 minutes before the following portion is added and wherein the addition is carried out at a temperature between 15 and 35° C.;

v) continue stirring the reaction mixture obtained in iv) for a period of between 16 and 30 hours at a temperature between 15 and 35° C.;

vi) adding water to the mixture obtained in step v) in an amount of between 400 and 750 milliliter per mole of 9,9-bis(hydroxymethyl)fluorene used and stirring for a period of time between 5 and 25 minutes at a temperature between 15 and 35° C.;

vi) separate the mixture obtained in step vi) in an organic layer and a water layer, obtain the organic layer and wash the organic layer with between 100 and 500 milliliter water per mole of 9,9-bis(hydroxymethyl) fluorene used;

vii) separate the mixture obtained in step vii) in an organic layer and a water layer, obtain the organic layer and remove the solvent by distillation to obtain crude 9,9-bis(methoxymethyl)fluorene;

viii) optionally recrystallize the crude 9,9-bis(methoxymethyl)fluorene from between 300 and 600 milliliter methanol per mole of 9,9-bis(hydroxymethyl)fluorene used and dry under vacuum to obtain 9,9-bis (methoxymethyl)fluorene.

DETAILED DESCRIPTION OF THE INVENTION

The present invention is related to a novel method of preparing 9,9-bis(methoxymethyl)fluorene.

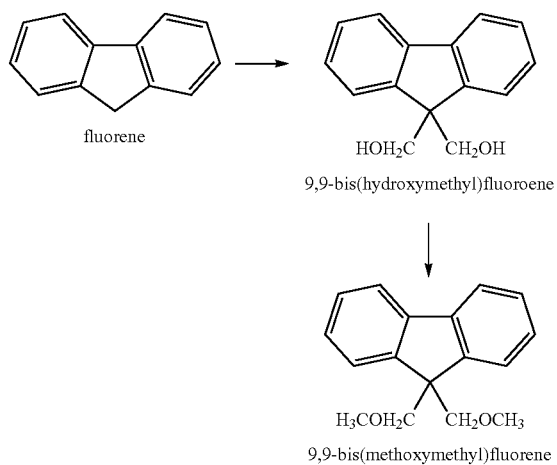

The above drawing shows schematically the two steps from fluorene to 9,9-bis(methoxymethyl)fluorene.

Step 1: Preparation of 9,9-bis(hydroxymethyl)fluorene

The present inventors have observed that by the addition of fluorene in solid form instead of as solution in DMSO the total amount of solvent needed during the synthesis and during the work up can be decreased dramatically while obtaining the desired 9,9-bis(hydroxymethyl)fluorene in high yield and high purity. The work up procedure is simplified by this method. This 9,9-bis(hydroxymethyl)fluorene can be used further in the synthesis of 9,9-bis (methoxymethyl)fluorene that can be used electron donor in Ziegler-Natta catalytic systems.

The key feature of the first aspect of the present invention is the use of fluorene in solid form.

In an embodiment of said first aspect, fluorene is added in the form of a powder. "Powder" as used in the present invention means: a solid substance composed of a large number of fine particles that may flow freely. It is in crystalline form. With fine particles is meant particles passing through a 50-100 mesh (viz. sieve of about 300 to about 150 micrometer). In other words, the particles have a diameter of between about 150 and about 300 micrometer, preferably at least 70%, more preferably 80%, more preferably 90%, even more preferably 95% of the particles have a diameter that lies in the range of between about 150 and about 300 micrometer. The use of fluorene in powder form has proven to be very effective and ensures a good reaction rate and homogeneity. A high yield is obtained.

It is also possible that fluorene is added in the form of a granulate or flakes. "Granulate" as used in the present invention means: a solid substance composed of a large number of large particles that may flow freely. It is in crystalline form. With large particles is meant particles having a diameter of between about 300 micrometer and about 4.0 millimeter, preferably at least 70%, more preferably 80%, more preferably 90%, even more preferably 95% of the particles have a diameter that lies in the range of between about 300 micrometer and about 4.0 millimeter.

In an embodiment of said first aspect, DMSO is present in an amount of at most 1250 milliliters per mole of fluorene used, preferably in an amount of at most 1000 milliliters per mole of fluorene used, more preferably in an amount of at most 500 milliliters per mole of fluorene used.

In an embodiment at least 500 milliliters of DMSO is used per mole of fluorene used.

In an embodiment, DMSO is present in an amount of at most 7.5, preferably at most 6, more preferably at most 4 milliliter per gram of fluorene, at least 3 milliliter per gram of fluorene.

The present inventors have observed that when fluorene is added as a solid and when maximizing the amount of DMSO, a good yield may be obtained and a high purity product, while ensuring less environmental and health issues by the reduced volume of DMSO.

In an embodiment of said first aspect, the molar ratio between fluorene and paraformaldehyde is between 1 to 1 and 1 to 3, preferably between 1 to 1.8 and 1 to 2.6. In an embodiment of said first aspect, paraformaldehyde is used in an amount of between 1.8 and 2.6 mole per mole of fluorene used. Most preferably, between 2.2 to 2.4 mole of paraformaldehyde per mole of fluorene is used, such as 2.3 mole. The present inventors have observed that such an amount leads to a good yield of the product and a low amount of side products.

In an embodiment of said first aspect, the sodium alkoxide is selected from sodium methoxide and sodium ethoxide, preferably sodium methoxide. In an embodiment of said first aspect, the sodium alkoxide is used as a sodium alkoxide solution in an alcoholic solution, preferably selected from sodium methoxide in methanol or sodium ethoxide in ethanol, more preferably sodium methoxide in methanol.

In an embodiment, the molar ratio between fluorene and sodium alkoxide is between 1 to 0.1 and 1 to 0.5, preferably between 1 to 0.2 and 1 to 0.3. The advantage thereof is that high yields are obtained and the formation of side product, such as the dimer product 9,9'-methylenedifluorene is reduced significantly.

In an embodiment, the sodium alkoxide is sodium methoxide, preferably as a solution in methanol, more preferably as a 25 to 35 wt. % solution in methanol wherein the percentage is a weight percentage based on the total weight of the solution. This solution is either prepared freshly or commercially obtained. When the concentration of the solution is lower, a lower yield will be obtained.

In an embodiment, the sodium alkoxide is present in the form of a solution in an alcohol, preferably in an amount of between 10 to 50 wt. %, preferably between 20 and 40 wt. %, between 25 and 35 wt. %, wherein the percentage is a weight percentage based on the total weight of the solution. This solution is either prepared freshly or commercially obtained. When the concentration of the solution is lower, a lower yield will be obtained.

In embodiments of said first aspect, said process comprises the steps a) to g) or a) to i) as discussed above. The present inventors have observed that this specific sequence of process steps provides good results.

In an embodiment of said first aspect, the acid used to quench the mixture in step e) is an inorganic acid, preferably hydrochloric acid, more preferably concentrated hydrochloric acid. However, a acidic solution of 10-20% may also be used.

In an embodiment of said first aspect, water is added during step f) in an amount of between 1250 and 5000 milliliters water per mole of fluorene used.

In an embodiment of said first aspect, the process is carried out at a temperature between 10 and 20° C. The advantage thereof is that the reaction rate is optimal and also that the production of the dimer side product, viz. 9,9'-methylenedifluorene is significantly reduced.

In an embodiment of said first aspect, fluorene is added over a period of between 5 and 30 minutes, preferably between 10 and 20 minutes, more preferably between 13 and 17 minutes.

In an embodiment of said first aspect, the reaction time after addition of fluorene is between 10 and 50 minutes, more preferably between 20 and 40 minutes, even more preferably between 25 and 35 minutes.

In an embodiment of said first aspect, the mixture of paraformaldehyde, dimethylsulfoxide and a sodium alkoxide is kept at a temperature between 10 and 20° C., preferably between 12 and 17° C. during the addition of fluorene.

In an embodiment of said first aspect, the mixture of paraformaldehyde, dimethylsulfoxide, sodium alkoxide and fluorene is kept at a temperature between 10 and 20° C., preferably between 12 and 17° C. during the reaction after completion of the addition of fluorene.

In an embodiment of said first aspect, the reaction is quenched to obtain a quenched reaction mixture by adding an acid, preferably hydrochloric acid, more preferably concentrated hydrochloric acid. Preferably, acid is used in an amount of between 0.05 to 0.15 milliliters per gram of fluorene used. In an embodiment, acid is used in an amount of between 10 and 20 milliliters per mole of fluorene used.

In an embodiment of said first aspect, the quenched reaction mixture is worked up by adding water of by adding the quenched reaction mixture to water in order to obtain a suspension of crude reaction product in water; preferably water is used in an amount of at least 5, preferably at least 10, preferably at most 20, preferably at most 15, more preferably at most 12 milliliters per gram of fluorene used.

In an embodiment of said first aspect, the suspension of crude reaction product is stirred between 10 and 50 minutes, more preferably between 20 and 40 minutes, even more preferably between 25 and 35 minutes.

In an embodiment of said first aspect, a crude reaction product is obtained after filtration of said suspension of crude reaction product.

In an embodiment of said first aspect, said crude reaction product is recrystallized from toluene, preferably in an amount of at most 8, preferably at most 6, more preferably at most 4 milliliter per gram of fluorene used. In an embodiment toluene is used in an amount of at most 1250 milliliters, more preferably at most 1000 milliliters, even more preferably at most 700 milliliters per mole, or even 667 milliliters per mole of fluorene.

In an embodiment of said first aspect, said recrystallization from toluene is carried out by heating the crude reaction product and toluene to a temperature between 60 and 110° C., preferably between 70 and 100° C., more preferably between 80 and 90° C., allowing the heated mixture to cool to room temperature, further cooling said mixture to a temperature between 0 and 20° C., preferably between 5 and 15° C., more preferably between 8 and 12° C. and maintaining the cooled mixture at said temperature for a period of time preferably between 30 and 240 minutes, more preferably between 60 and 180 minutes, even more preferably between 90 and 150 minutes to obtain solid 9,9-bis(hydroxymethyl)fluorene.

In an embodiment of said first aspect, the solid 9,9-bis(hydroxymethyl)fluorene is obtained by filtration. In an embodiment of said first aspect, the solid 9,9-bis(hydroxymethyl)fluorene is further washed, preferably with toluene, and optionally dried under vacuum to obtain 9,9-bis(hydroxymethyl)fluorene.

Step 2: Preparation of
9,9-bis(methoxymethyl)fluorene

The present invention is related in a second aspect to a novel method of preparing 9,9-bis(methoxymethyl)fluorene. The method according to the prior art adds the total volume of dimethyl sulfate, either at once or drop wise, during one single period of time. The present inventors have observed that it is advantageous to add the total amount of dimethyl sulfate in at least three discrete portions wherein there is a reaction or wait time, preferably of at least 60 minutes, in between the addition of each portion. The reason for this is if it is added in one lot dimethyl sulfate partly will decompose and also reduce strength of alkali not allowing further reaction happening. The present inventor have inventively found out that if DMS is added too slow or drop wise it will hydrolyze and required more, which is undesirable. The present invention solves this problem by adding it in lots or portions. In an embodiment DMS is first diluted with a solvent, such as toluene, prior to being added to the reaction mixture.

The two aspects of the present invention may be combined by first preparing 9,9-bis(hydroxymethyl)fluorene prepared according to the process in the first aspect of the present invention and subsequently preparing 9,9-bis(hydroxymethyl)fluorene. However, 9,9-bis(hydroxymethyl)fluorene may also be obtained by other methods.

In an embodiment of said second aspect, as the alkali metal hydroxide sodium hydroxide is used, preferably as a 40 to 50 wt. % solution in water. The advantage thereof is that the reaction rate is higher when the concentration of the hydroxide solution is in this range. As the concentration decreases, the reaction rate also decreases.

In an embodiment of said second aspect, as the tetraalkylammonium halide tetra-n-butylammonium bromide is used. This compound provides a good effect and is readily available commercially.

In an embodiment of said second aspect, dimethyl sulfate is added in at least four portions, such as in at least five portions. The advantage thereof is that the decomposition of DMS is further reduced In an embodiment of said second aspect, dimethyl sulfate is added in a total amount of between 2 and 6 moles per mole of 9,9-bis(hydroxymethyl)fluorene used. The advantage thereof is that on the one hand a good yield and purity is obtained and on the other hand the amount is limited so as to decrease the costs.

In an embodiment of said second aspect, as the solvent toluene is used. The advantage thereof is that the product is very soluble in toluene. Another solvent may be used and selected by a person skilled in the art, based on the solubility of the product.

In embodiment of said second aspect, said process comprises the steps of i) to vii) or step i) to viii) as discussed above. The present inventors have observed that this specific sequence of process steps provides good results.

In an embodiment of said second aspect, a solution of between 40 and 60 wt. %, preferably between 45 and 55 wt. % of alkali metal (preferably sodium) hydroxide in water is used.

In an embodiment of said second aspect, the molar ratio between alkali metal (preferably sodium) hydroxide and 9,9-bis(hydroxymethyl)fluorene is between 2.5 to 1 and 7.5 to 1, preferably between 4 to 1 and 6 to 1.

In an embodiment of said second aspect, tetra-n-butylammonium bromide is used in an amount of between 0.005 and 0.025 mole per mole of 9,9-bis(hydroxymethyl)fluorene used.

In an embodiment of said second aspect, toluene is used in an amount of between 800 and 1500 milliliter per mole of 9,9-bis(hydroxymethyl)fluorene used.

In an embodiment of said second aspect, the mixture of step ii) is stirred for a period of between 1 and 5 hours, preferably between 2 and 4 hours.

In an embodiment of said second aspect, the mixture of step ii) is stirred at a temperature between 15 and 30° C., preferably between 20 and 25° C.

In an embodiment of said second aspect, the dimethyl sulfate is added in a total amount of between 2 and 6 moles, preferably between 3 and 5, more preferably between 3.5 and 4.5 mole, per mole of 9,9-bis(hydroxymethyl)fluorene used.

In an embodiment of said second aspect, the dimethyl sulfate is added in several portions, preferably substantially equal portions (viz. portions that have weights that are within +/−10% of each other). Preferably, between 3 to 6 portions, more preferably between 4 to 5 portions are used. The present inventor has found out that when using two portions, the reaction does not go to completion and more DMS is required which is undesirable.

In an embodiment of said second aspect, each portion of dimethyl sulfate is added over a period of between 15 and 60 minutes, preferably 30 and 45 minutes.

In an embodiment of said second aspect, the reaction mixture after a portion of dimethyl sulfate is added is stirred for a period of between 60 and 120 minutes, preferably between 80 and 100 minutes, before the following portion of dimethyl sulfate is added. The conversion is checked by means of TLC (EtAc+Heptane-20+80). If the reaction is not complete it may be stirred for another few hours at room temperature.

In an embodiment of said second aspect, the addition of the portions of dimethyl sulfate is carried out at a temperature between 15 and 35° C., preferably between 20 and 25° C.

In an embodiment of said second aspect, after the addition of the final portion of dimethyl sulfate, the mixture is stirred for a period of between 16 and 30 hours, preferably between 20 and 25 hours, preferably at a temperature between 15 and 35° C., more preferably between 20 and 25° C.

In an embodiment of said second aspect, water is added for work up of the reaction mixture in an amount of between 400 and 700 milliliter water, preferably between 500 and 600 milliliter per mole of 9,9-bis(hydroxymethyl)fluorene used.

In an embodiment of said second aspect, the worked up reaction mixture comprising water is stirred for a period of time between 5 and 25 minutes, preferably between 10 and 15 minutes.

In an embodiment of said second aspect, the worked up reaction mixture comprising water is stirred at a temperature between 15 and 35° C., preferably between 20 and 25° C.

In an embodiment of said second aspect, remove the organic layer from the water layer and wash the organic layer with between 300 and 600 milliliter water, preferably between 400 and 500 milliliters water per mole of 9,9-bis (hydroxymethyl)fluorene used.

In an embodiment of said second aspect, remove the organic layer from the water layer and remove the solvent by distillation to obtain crude 9,9-bis(methoxymethyl)fluorene.

In an embodiment of said second aspect, optionally recrystallize the crude 9,9-bis(methoxymethyl)fluorene from between 400 and 700 milliliter methanol, preferably between 500 and 600 milliliter per mole of 9,9-bis(hydroxymethyl)fluorene used and dry under vacuum to obtain 9,9-bis(methoxymethyl)fluorene.

The present invention is further elucidated by means of the following non-limiting examples.

EXAMPLES

Materials and Methods

All materials mentioned are obtained by commercial supplier and are readily available.

HPLC was measured using as mobile Phase-A 0.02% orthophosphoric acid and using as mobile Phase-B Acetonitrile. The HPLC Column used was a Hypersil BDS, C18, (250×4.6)mm, 5μ. The measurement is done at a wavelength of 223 nm; a column oven temperature of 400° C.; an injection volume of 10 μl; a flow rate of 1.0 mL/min. As a diluent acetonitrile is used.

Method of Preparing
9,9-bis(hydroxymethyl)fluorene, Suitable for Use in
Example 1

Dimethylsulfoxide (DMSO) (400 ml) and paraformaldehyde (PF) (40 gram) were charged into a round bottom flask, mixed and cooled to a temperature of 13-15° C. Subsequently, sodium methoxide 30% solution (26 gram) was added to this mixture. Gradually fluorene in powder form (100 gram) was added to above reaction mixture over a period of 15 minutes, while the temperature was maintained at 14-16° C. It was observed that most of the paraformaldehyde dissolves instantly upon addition of the fluorene. The resulting mixture was stirred for 30 minutes while the temperature was maintained at 14-16° C. The resulting mixture was a clear pale yellow solution.

Subsequently, concentrated HCl (8-10 ml) was added to the obtained solution until al neutral pH was reached in order to stop the reaction. The following work up was carried out for the reaction mixture: a large 3-5 liter round bottom flask was charged with water (1200 ml). The reaction mixture was slowed added to the water under stirring. The resulting mixture was stirred for 30 minutes at room temperature. The solid crude reaction product was obtained by filtration.

To the crude product toluene (350 ml) was added. The mixture was heated to 80-90° C. The heating was stopped and the mixture was allowed to return to room temperature. Then the mixture was further cooled to 10° C. and maintained at that temperature for 2 hours. The solid product was filtered and washed with chilled toluene (two times 25 ml). The solid product was kept under vacuum till the toluene was completely removed from the product. The wet weight of the solid product was 150 gram.

The product is then dried at 60-70° C. and weighed again. The dry weight was 85-93 gram. The yield was 69%. The purity of the product as determined by HPLC was >98%. The melting point was 139-144° C.

Different Method of Preparing 9,9-bis(hydroxymethyl)fluorene, Suitable for Use in Example 1

Dimethylsulfoxide (DMSO) (300 ml) and paraformaldehyde (PF) (25 gram) were charged into a round bottom flask, mixed and cooled to a temperature of 13-15° C. Subsequently, sodium methoxide 30% solution (3.5 gram) was added to this mixture.

A solution of fluorene (50 gram) in DMSO (300 ml) was added to above reaction mixture over a period of 1-2 minutes, while the temperature was maintained at 14-16° C. The resulting mixture was stirred for 15 minutes while the temperature was maintained at 14-16° C. The resulting mixture was a clear pale yellow solution.

Subsequently, concentrated HCl (5-10 ml) was added to the obtained solution until al neutral pH (pH 6-7) was reached in order to stop the reaction. The following work up was carried out for the reaction mixture: a large 3-5 liter round bottom flask was charged with water (1200 ml). The reaction mixture was slowed added to the water under stirring. The resulting mixture was stirred for 15-30 minutes at room temperature. The crude reaction product was obtained by extraction with ethyl acetate.

The organic phase is dried and distilled under vacuum. The residue was crystallized in 200 ml toluene to get the product as off white crystals. The dry weight was 25 gram. The yield was 30%. The purity of the product as determined by HPLC was >98%.

Example 1: Preparation of 9,9-bis(methoxymethyl)fluorene

Sodium hydroxide (NaOH) (100 gram) was dissolved in water (100 ml) in a 2 liter round bottom flask under stirring. The reaction mixture was allowed to cool to room temperature. To this were added 9,9-bis(hydroxymethyl)fluorene (100 gram), tetrabutylammonium bromide (2 gram) and toluene (500 ml). The resulting mixture was stirred at room temperature for 2-3 hours. At this stage the reaction mixture changed in nature and had become a thick paste.

The addition of the methylation agent, dimethyl sulfate (DMS) was carried out in four equal lots, each at a temperature of between 20-30° C. Each lot was added over a period of between 30-40 minutes in a drop wise manner. After each addition the resulting mass was stirred for 90 minutes before starting the addition of another lot. After all lots were added, the mass was stirred at the same temperature for another 20-24 hours. The solid paste dissolved and the color of the toluene layer became pale yellow.

Water (250 ml) was then added and the mixture was stirred for 15 minutes. The organic layer was separated and washed with water (200 ml). Toluene was distilled and traces thereof were removed by vacuum. To the solid residue methanol (200 ml) was added and this was refluxed for 15-30 minutes. The heating was stopped and the reaction mixture was cooled to 10° C. and maintained at that temperature for 2 hours. The product was filtered and washed with chilled methanol (two times 25 ml). The wet weight was 85 gram. The product was then dried 50-60° C. under vacuum to give a dry weight of 75-80 gram. The purity observed by HPLC was >99%. The yield was 80%.

Comparative Example 1: Preparation of 9,9-bis(methoxymethyl)fluorene

Sodium hydroxide (NaOH) (50 gram) was dissolved in water (50 ml) in a 1 liter round bottom flask under stirring. The reaction mixture was allowed to cool to room temperature. To this was added 9,9-bis(hydroxymethyl)fluorene (50 gram), tetrabutylammonium bromide (1 gram) and toluene (250 ml). The resulting mixture was stirred at room temperature for 2-3 hours. To the reaction mass dimethyl sulfate (DMS)(115 gram) was added in one portion, at a temperature of between 20-30° C. The mass was stirred at the same temperature for another 20-24 hours. Water (125 ml) was then added and the mixture was stirred for 15 minutes. The organic layer was separated and washed with water (100 ml). Toluene was distilled and traces thereof were removed by vacuum. To the solid residue methanol (100 ml) was added and this was refluxed for 15-30 minutes. The heating was stopped and the reaction mixture was cooled to 10° C. and maintained at that temperature for 2 hours. The product was filtered and washed with chilled methanol. The product was then dried to give a dry weight of 25 gram. The yield was 44%.

The above results clearly show that with the process according to the present invention good yields and purity may be obtained. Hence one or more of the above aims are achieved by the present invention as disclosed in the appended claims.

It is noted that the invention relates to all possible combinations of features recited in the claims. Features described in the description may further be combined.

Although the invention has been described in detail for purposes of illustration, it is understood that such detail is solely for that purpose and variations can be made therein by those skilled in the art without departing from the spirit and scope of the invention as defined in the claims. It is further noted that the invention relates to all possible combinations of features described herein, preferred in particular are those combinations of features that are present in the claims.

The invention claimed is:

1. A process for the synthesis of 9,9-bis(methoxymethyl)fluorene from 9,9-bis(hydroxymethyl)fluorene comprising:
   providing an alkali metal hydroxide solution,
   mixing said solution with tetraalkylammonium halide, 9,9-bis(hydroxymethyl)fluorene and a solvent and adding dimethyl sulfate to obtain 9,9-bis(methoxymethyl)fluorene,
   wherein dimethyl sulfate is added in at least three portions wherein after adding a first portion, the reaction mixture is stirred for a period of at least 60 minutes before the additional portions are added.

2. A process according to claim 1, wherein sodium hydroxide is used as the alkali metal hydroxide.

3. A process according to claim 1, wherein tetra-n-butylammonium bromide is used as the tetraalkylammonium halide.

4. A process according to claim 1, wherein dimethyl sulfate is added in at least four portions.

5. A process according to claim 1, wherein dimethyl sulfate is added in a total amount of between 2 and 6 moles per mole of 9,9-bis(hydroxymethyl)fluorene used.

6. A process according to claim 1, wherein toluene is used as the solvent.

7. A process according to claim 1, comprising the steps of
   i) providing a solution of sodium hydroxide in water;
   ii) adding to the solution of step i) 9,9-bis(hydroxymethyl)fluorene, tetraalkylammonium halide and a solvent;
   iii) stirring the mixture obtained in step ii);
   iv) adding dimethyl sulfate in at least three portions, wherein after adding a first portion, the resulting reaction mixture obtained is stirred for a certain period of time before the additional portions are added;
   v) continually stirring the reaction mixture obtained in iv);
   vi) adding water to the mixture obtained in step v) and stirring;
   vii) separating the mixture obtained in step vi) in an organic layer and a water layer, obtaining the organic layer and washing the organic layer with water;
   viii) separating the mixture obtained in step vii) in an organic layer and a water layer, obtaining the organic layer and removing the solvent to obtain crude 9,9-bis(methoxymethyl)fluorene.

8. A process according to claim 7, wherein the crude 9,9-bis(methoxymethyl)fluorene obtained in step vii) is recrystallized to obtain 9,9-bis(methoxymethyl)fluorene.

9. A process according to claim 7, wherein in step iv) each portion of dimethyl sulfate is added over a period of between 15 and 60 minutes.

10. A process according to claim 7, wherein in step iv) between the addition of each portion the reaction mixture is stirred for a period of between 60 and 120 minutes.

11. A process according to claim 7, wherein step v) is carried out for a period of between 16 and 30 hours.

12. A process according to claim 1, wherein step iv) and/or step v) are carried out at a temperature of between 15 and 35° C.

13. A process according to claim 1, comprising the steps of
   i) providing a solution of between 40 and 50 wt. % of sodium hydroxide in water so that between 2.5 and 7.5 mole of sodium hydroxide is present per mole of 9,9-bis(hydroxymethyl)fluorene used;
   ii) adding to the solution in step i) 9,9-bis(hydroxymethyl)fluorene, tetra-n-butylammonium bromide in an amount of 0.005 and 0.025 mole per mole of 9,9-bis(hydroxymethyl)fluorene used and adding toluene in an amount of between 800 and 1500 milliliter per mole of 9,9-bis(hydroxymethyl)fluorene used;
   iii) stirring the mixture obtained in step ii) for a period of between 1 and 5 hours at a temperature between 15 and 30° C.;
   iv) adding dimethyl sulfate in a total amount of between 2 and 6 moles per mole of 9,9-bis(hydroxymethyl)fluorene in between 3 to 6 portions, wherein each portion is added over a period of between 15 and 60 minutes and wherein after adding a first portion, the resulting reaction mixture is stirred for a period of between 60 and 120 minutes before the additional portions are added and wherein the addition is carried out at a temperature between 15 and 35° C.;
   v) continuing to stir the reaction mixture obtained in iv) for a period of between 16 and 30 hours at a temperature between 15 and 35° C.;
   vi) adding water to the mixture obtained in step v) in an amount of between 400 and 750 milliliter per mole of 9,9-bis(hydroxymethyl)fluorene used and stirring for a period of time between 5 and 25 minutes at a temperature between 15 and 35° C.;
   vii) separating the mixture obtained in step vi) into an organic layer and a water layer, obtaining the organic layer and washing the organic layer with between 100 and 500 milliliter water per mole of 9,9-bis(hydroxymethyl)fluorene used;
   viii) separating the mixture obtained in step vii) in an organic layer and a water layer, obtain the organic layer and remove the solvent by distillation to obtain crude 9,9-bis(methoxymethyl)fluorene;
   ix) optionally recrystallizing the crude 9,9-bis(methoxymethyl)fluorene from between 300 and 600 milliliter methanol per mole of 9,9-bis(hydroxymethyl)fluorene used and drying under vacuum to obtain 9,9-bis(methoxymethyl)fluorene.

14. The process according to claim 2, wherein the sodium hydroxide used is as a 40 to 50 wt. % solution in water.

* * * * *